(12) United States Patent
Young et al.

(10) Patent No.: US 8,840,665 B2
(45) Date of Patent: Sep. 23, 2014

(54) METHOD OF TENDON REPAIR WITH AMNION AND CHORION CONSTRUCTS

(75) Inventors: Robin R. Young, Wayne, PA (US); Richard M. Jay, Philadelphia, PA (US)

(73) Assignee: Liventa Bioscience, Inc., Conshohocken, PA (US)

( * ) Notice: Subject to any disclaimer, the term of this patent is extended or adjusted under 35 U.S.C. 154(b) by 493 days.

(21) Appl. No.: 13/157,643

(22) Filed: Jun. 10, 2011

(65) Prior Publication Data

US 2011/0307059 A1 Dec. 15, 2011

Related U.S. Application Data

(60) Provisional application No. 61/353,717, filed on Jun. 11, 2010.

(51) Int. Cl.
*A61F 2/08* (2006.01)
*A61L 27/36* (2006.01)

(52) U.S. Cl.
CPC ......... *A61L 27/3604* (2013.01); *A61L 2430/10* (2013.01); *A61L 27/3662* (2013.01); *A61F 2/08* (2013.01)
USPC ...................................................... 623/13.17

(58) Field of Classification Search
CPC ....................................................... A61F 2/08
USPC ............................. 623/13.7–14.12
See application file for complete search history.

(56) References Cited

U.S. PATENT DOCUMENTS

| 4,400,833 A | 8/1983 | Kurland |
| 4,585,458 A | 4/1986 | Kurland |
| 5,612,028 A | 3/1997 | Sackier et al. |
| 6,087,552 A | 7/2000 | Gregory |
| 6,152,142 A | 11/2000 | Tseng |
| 6,326,019 B1 | 12/2001 | Tseng |
| 6,740,122 B1 | 5/2004 | Pajotin |
| 6,872,384 B1 * | 3/2005 | Franklin et al. ............ 424/78.18 |
| 7,160,333 B2 | 1/2007 | Plouhar et al. |
| 7,244,444 B2 | 7/2007 | Bates |
| 7,255,879 B2 | 8/2007 | Hariri |
| 8,105,634 B2 | 1/2012 | Liu et al. |
| 8,129,359 B2 * | 3/2012 | Herzberg et al. ............... 514/57 |
| 8,323,701 B2 | 12/2012 | Daniel et al. |

(Continued)

FOREIGN PATENT DOCUMENTS

| WO | 0073421 A2 | 12/2000 |
| WO | 2009044408 A1 | 4/2009 |
| WO | 2009132186 A1 | 10/2009 |

OTHER PUBLICATIONS

U.S. Appl. No. 13/804,731 by Young, filed Mar. 14, 2013.

(Continued)

*Primary Examiner* — Suzette J Gherbi

(74) *Attorney, Agent, or Firm* — Panitch Schwarze Belisario & Nadel LLP

(57) ABSTRACT

It is described a construct for use in surgical repair of tendon. The construct contains at least one layer of human amnion and chorion tissues and is generally cylindrical with a C-shaped cross-section to allow for ease of implantation over the tendon. Methods for preparing the construct is described. In addition, an improved method for surgical repair of a damaged or diseased tendon using the construct is also described. The improved method reduces adhesions, scar formation, inflammation and risk of post-operative infection.

19 Claims, 4 Drawing Sheets

(56) References Cited

U.S. PATENT DOCUMENTS

| | | | |
|---|---|---|---|
| 2001/0050083 A1 | 12/2001 | Marchitto et al. | |
| 2001/0053839 A1 | 12/2001 | Noishiki et al. | |
| 2002/0026092 A1 | 2/2002 | Buckberg et al. | |
| 2003/0023316 A1 | 1/2003 | Brown et al. | |
| 2003/0187515 A1 | 10/2003 | Hariri et al. | |
| 2003/0212456 A1 | 11/2003 | Lipchitz et al. | |
| 2004/0048796 A1 | 3/2004 | Hariri et al. | |
| 2004/0181240 A1 | 9/2004 | Tseng et al. | |
| 2005/0113938 A1 | 5/2005 | Jamiolkowski et al. | |
| 2005/0137704 A1* | 6/2005 | Steenlage | 623/13.14 |
| 2005/0186193 A1* | 8/2005 | Mishra | 424/93.72 |
| 2005/0214259 A1 | 9/2005 | Sano et al. | |
| 2006/0153928 A1 | 7/2006 | Kinoshita et al. | |
| 2007/0021762 A1 | 1/2007 | Liu et al. | |
| 2007/0061013 A1 | 3/2007 | Cauthen III et al. | |
| 2007/0191849 A1 | 8/2007 | ElAttrache et al. | |
| 2007/0198059 A1 | 8/2007 | Patel et al. | |
| 2007/0233135 A1 | 10/2007 | Gil et al. | |
| 2007/0270953 A1* | 11/2007 | Trieu | 623/17.11 |
| 2008/0027477 A1 | 1/2008 | Obermiller et al. | |
| 2008/0046095 A1 | 2/2008 | Daniel | |
| 2008/0188766 A1 | 8/2008 | Gertner | |
| 2008/0193554 A1 | 8/2008 | Dua et al. | |
| 2008/0269899 A1 | 10/2008 | Horton | |
| 2008/0274184 A1 | 11/2008 | Hunt | |
| 2009/0125119 A1 | 5/2009 | Obermiller et al. | |
| 2009/0142396 A1 | 6/2009 | Odar et al. | |
| 2009/0204228 A1 | 8/2009 | Hiles | |
| 2010/0104539 A1 | 4/2010 | Daniel et al. | |
| 2010/0106178 A1 | 4/2010 | Obermiller et al. | |
| 2010/0161345 A1 | 6/2010 | Cain et al. | |
| 2010/0228335 A1 | 9/2010 | Schorgl et al. | |
| 2010/0324693 A1* | 12/2010 | Hardenbrook | 623/21.11 |
| 2011/0152898 A1 | 6/2011 | Kochevar et al. | |
| 2011/0319989 A1 | 12/2011 | Lane et al. | |
| 2012/0010708 A1 | 1/2012 | Young et al. | |
| 2012/0010727 A1 | 1/2012 | Young et al. | |
| 2012/0020933 A1* | 1/2012 | Young et al. | 424/93.7 |
| 2012/0035743 A1 | 2/2012 | Young et al. | |
| 2012/0035744 A1 | 2/2012 | Young et al. | |
| 2012/0078378 A1 | 3/2012 | Daniel et al. | |
| 2012/0083900 A1 | 4/2012 | Samaniego et al. | |
| 2012/0141595 A1 | 6/2012 | Tseng et al. | |
| 2012/0179176 A1 | 7/2012 | Wilson et al. | |
| 2013/0156863 A1 | 6/2013 | Tseng et al. | |
| 2013/0211511 A1 | 8/2013 | Young | |
| 2013/0344163 A1 | 12/2013 | Tseng et al. | |

OTHER PUBLICATIONS

U.S. Appl. No. 13/804,785 by Young, filed Mar. 14, 2013.

U.S. Appl. No. 13/790,712 by Young, filed Mar. 8, 2013.

U.S. Appl. No. 13/790,703 by Young, filed Mar. 8, 2013.

Office Action issued Jun. 10, 2013 in U.S. Appl. No. 13/179,966.

Ozgenel et al, "Effects of human amniotic fluid on peripheral nerve scarring and regeneration in rats," Journal of Neurosurgery, vol. 98, pp. 371-377 (2003).

Office Action issued Jul. 15, 2013 in U.S. Appl. No. 13/195,189 by Young.

Sorsby et al, "Further Experience with Amniotic Membrane Grafts in Caustic Burns of the Eye", British Journal of Ophthalmology, vol. 31, No. 7, pp. 409-418 (1947).

Kim et al, "Transplantation of Preserved Human Amniotic Membrane for Surface Reconstruction in Severely Damaged Rabbit Corneas", Cornea, vol. 14, No. 5, pp. 473-484 (1995).

Kruse et al, "Cryopreserved human amniotic membrane for ocular surface reconstruction", Graefe's Archive for Clinical and Experimental Ophthalmology, vol. 238, pp. 68-75 (2000).

Solomon et al, "Suppression of interleuken 1alpha and interleukin 1beta in human limbal epithelial cells cultured on the amniotic membrane stromal matrix", British Journal of Ophthalmology, vol. 85, No. 4, pp. 444-449 (2001).

Hao et al, "Identification of Antiangiogenic and Antiinflammatory Proteins in Human Amniotic Membrane", Cornea, vol. 19, No. 3, pp. 348-352 (2000).

Kim et al, "Amniotic Membrane Patching Promotes Healing and Inhibits Proteinase Activity on Wound Healing Following Acute Corneal Alkali Burn", Experimental Eye Research, vol. 70, No. 3, pp. 329-337 (2000).

Dua, "Perspective—Amniotic Membrane Transplantation", The British Journal of Ophthalmology, vol. 83, No. 6, pp. 748-752 (1999).

Tsai et al, "Human Allograft Limbal Transplantation for Corneal Surface Reconstruction", Cornea, vol. 13, No. 5, pp. 389-400 (1994).

Chao et al, "A New Method of preventing Adhesions. The Use of Amnioplastin after Craniotomy", The British Medical Journal, vol. 517, No. 1 (1940).

Trelford et al, "The amnion in surgery, past and present", American Journal of Obstetrics & Gynecology, vol. 134, pp. 833-845 (1979).

King et al, "Elafin in Human Endometrium: An Antiprotease and Antimicrobial Molecule Expressed during Menstruation", The Journal of Clinical Endocrinology & Metabolism, vol. 88, pp. 4426-4431 (2003).

Buhimschi et al, "The novel antimicrobial peptide beta3-defensin is produced by the amnion: A possible role of the fetal membranes in innate immunity of the amniotic cavity", American Journal of Obstetrics & Gynecology, vol. 191, pp. 1678-1687 (2004).

Krisanaprakornkit et al, "Expression of the Peptide Antibiotic Human beta-Defensin 1 in Cultured Gingival Epithelial Cells and Gingival Tissue", Infection and Immunity, vol. 66, pp. 4222-4228 (1998).

Harder et al, "Mucoid *Pseudomonas aeruginosa*, TNF-alpha, and IL-1 beta, but not IL-6, Induce Human beta-Defensin-2 in Respiratory Epithelia", American Journal of Respiratory Cell and Molecular Biology, vol. 22, pp. 714-721 (2000).

King et al, "Expression of Natural Antimicrobials by Human Placenta and Fetal Membranes", Placenta, vol. 28, No. 2, pp. 161-169 (2007).

Lee et al, "Suppression of TGF-beta signaling in both normal conjunctival fibroblasts and pterygial body fibroblasts by amniotic membrane", vol. 20, No. 4, pp. 325-334 (2000).

Tseng et al, "Suppression of transforming growth factor-beta isoforms, TGF-beta receptor type II, and myofibroblast differentiation in cultured human corneal and limbal fibroblasts by amniotic membrane matrix", vol. 179, No. 3, pp. 325-335 (1999).

Niknejad et al, "Properties of the amniotic membrane for potential use in tissue engineering", European Cells and Materials Journal, vol. 15, pp. 88-99 (2008).

Demirkan et al, "The use of amniotic membrane in flexor tendon repair: an experimental model", Archives of Orthopaedic and Trauma Surgery, vol. 122, No. 7, pp. 396-399 (2002).

Peacock, "Wound Repair", 3rd Ed., WB Saunders & Co., pp. 263-331 (1984).

King et al, "Innate immune defences in the human endometrium", Reproductive Biology and Endocrinology, vol. 1, No. 116, pp. 1-8 (2003).

Burman et al, "Ophthalmic applications of preserved human amniotic membrane: A review of current indications", Cell and Tissue Banking, vol. 5, pp. 161-175 (2004).

Barabino et al, "Role of Amniotic Membrane Transplantation for Conjunctival Reconstruction in Ocular-Cicatricial Pemphigoid", Ophthalmology, vol. 110, No. 3, pp. 474-480 (Mar. 2003).

Kobayashi et al, "Multi-layer Amniotic Membrane Graft for Pterygium in a Patient with Xeroderma Pigmentosum", Japanese Journal of Opthalmology, vol. 45, pp. 496-498 (2001).

Hanada et al, "Multilayered Amniotic Memrane Transplantation for Severe Ulceration of the Cornea and Sclera", American Journal of Ophthalmology, vol. 131, No. 3, pp. 324-331 (Mar. 2001).

Meller et al, "Conjunctival Epithelial Cell Differentiation on Amniotic Membrane", Investigative Ophthalmology & Visual Science, vol. 40, No. 5, pp. 878-886 (Apr. 1999).

Rinastiti et al, "Histological evaluation of rabbit gingival wound healing transplanted with human amniotic membrane", International Journal of Oral & Maxillofacial Surgery, vol. 35, pp. 247-251 (2006).

(56) References Cited

OTHER PUBLICATIONS

Schwab, "Cultured corneal epithelia for ocular surface disease", Transactions of the American Ophthalmological Society, No. 135, pp. 891-986 (1999).
Yang et al, "New skin-equivalent model from de-epithelialized amnion membrane", Cell Tissue Research, vol. 326, pp. 69-77 (2006).
U.S. Appl. No. 13/767,204 by Young, filed Feb. 14, 2013.
U.S. Appl. No. 13/767,210 by Young, filed Feb. 14, 2013.
U.S. Appl. No. 13/767,215 by Young, filed Feb. 14, 2013.
U.S. Appl. No. 13/767,221 by Young, filed Feb. 14, 2013.
U.S. Appl. No. 13/767,224 by Young, filed Feb. 14, 2013.
Office Action issued Dec. 31, 2012 in U.S. Appl. No. 13/177,177.
Office Action issued May 23, 2013 in U.S. Appl. No. 13/177,177.
Office Action issued Nov. 15, 2013 in U.S. Appl. No. 13/179,966.
Office Action issued Nov. 21, 2013 in U.S. Appl. No. 13/178,980.
Khalid et al, "Suturing of lacerations of skeletal muscle," J. Hand Microsurg., vol. 1, No. 1, pp. 54-59 (Jun. 2009).
Kragh et al, "Suturing of lacerations of skeletal muscle," The Journal of Bone and Joint Surgery, vol. 87, No. 9, pp. 1303-1305 (Sep. 2005).
Office Action issued Nov. 27, 2013 in U.S. Appl. No. 13/177,177.
Office Action issued Nov. 29, 2013 in U.S. Appl. No. 13/195,189.
Office Action issued Dec. 3, 2013 in U.S. Appl. No. 13/790,703.
Office Action issued Dec. 20, 2013 in U.S. Appl. No. 13/767,221.
Novitzky et al, "The Transplantation and Replacement of Thoracic Organs," Chapter 11, pp. 81-87 (1990).
Jabareen et al, "Relation between mechanical properties and microstructure of human fetal membranes: An attempt towards a quantitative analysis," Eur. J. of Ob. Gyn. Reprod. Biol., vol. 144S, pp. S134-S141 (2009).
Maisch et al, "Guideline on the Diagnosis and Management of Pericardial Diseases," Eur. Heart J., pp. 1-28 (2004).
Office Action issued Feb. 12, 2014 in U.S. Appl. No. 13/198,330 by Young.
U.S. Appl. No. 14/290,391 by Young, filed May 29, 2014.
Office Action issued Apr. 17, 2014 in U.S. Appl. No. 13/178,980.
Office Action issued May 28, 2014 in U.S. Appl. No. 13/767,210.

\* cited by examiner

METHOD OF TENDON REPAIR WITH AMNION AND CHORION CONSTRUCTS

CROSS-REFERENCE TO RELATED APPLICATIONS

This application is entitled to priority pursuant to 35 U.S.C. §119(e) to U.S. Provisional Patent Application No. 61/353,717, filed Jun. 11, 2010 which is hereby incorporated by reference herein in its entirety.

BACKGROUND OF THE INVENTION

1. Field of Invention

This invention relates to methods for reducing inflammation, inhibiting fibrosis, scarring, fibroblast proliferation, post-operative infection while also promoting smooth gliding of the tendon and healing using processed amnion and/or chorion tissues as part of a surgical intervention treatment program to repair damaged or diseased tendons.

2. Background of the Invention

Tendons are a type of regularly arranged dense soft, connective tissue that bridges and attaches muscles to bone. This fibrous and flexible tissue is also called sinew. Tendons are comprised of type I collagen (80% by weight) that are arranged in fibrils. The fibrils form a fascicle, which includes the basic tendon fibril and also fibroblasts in parallel rows. Covering the tendon is a thin fascia tissue membrane. Tendons also contain some elastin fibers, a proteoglycan matrix and proteinaceous filler between the connective tissue fibers.

When tendons are ruptured due to trauma or surgical intervention, they typically take longer than, for example, bone to heal. Tendons have poor spontaneous regenerative capabilities and complete regeneration is almost never achieved despite intensive remodeling. One of the reasons for this is the absence of tendon sheathing. Tendons have a thin fascia membrane cover which protects the tendon while also allowing it to move and slide freely against adjacent tissue structures like muscle, skin or bone.

Patients whose tendon(s) have been ruptured experience pain, reduced mobility, reduced lubrication between the articulating and adjacent tissues and a heightened risk of post trauma scarring, adhesions and pain. A primary cause of this is damage to the protective sheathing of the tendon.

When a tendon sheath is injured, stressed or traumatized, the natural response of the damaged tissue is to increase the tensional forces thus making a "sling" over the injured tendon. The tendon sheath also responds to trauma by "gluing" affected areas of the site of tendon injury. After the tendon trauma, the fascia sheathing sometimes "forgets" to unglue and patients then experience a layer of tendon and adhesion to the tendon injury site. In those cases, the tendon no longer slides and adjacent structures painfully tether and tug at each other.

A classic example of this phenomenon is called "trigger finger". In this case the tendon fascia sheath has narrowed and begun to "glue" onto the finger tendon. The membrane then becomes inflamed (tenosynovitis). That inflammation then causes the tendon to swell, which constricts further the ability of the tendon to glide between adjacent structures and the tendon no longer moves smoothly through its sheath. In the case of "trigger finger" the finger locks into an upward position.

In other cases, during the healing process following a traumatically injured tendon, the body may deposit an excess amount of fibrous collagen at the site of injury. Physicians refer to this excess proliferation of fibrous collagen as surgical adhesions or scar tissue formation at the site of injury.

The surgical option offers a significantly smaller risk of re-rupture compared to traditional non-operative management, e.g., 5% vs 15% for treatment of acute Achilles tendon ruptures. See Richter J et al., *Zentralbl Chir*, 1994, 119 (8): 538-44. However surgery imposes much higher relative risks of perioperative mortality and morbidity, e.g. infection including MRSA, bleeding, deep vein thrombosis, lingering anesthesia effects, stiffness, suture reaction, persistent pain or weakness after the injury and repair, etc.

Peritendonous adhesions are a contributor to poor outcomes in patients undergoing tendon surgery. Following tendon repair surgery, fibroblasts from surrounding tissues migrate into the wound during the healing process leading to the formation of scar tissue. Peacock E K. In: *Peacock E K (ed) Wound repair*. W B Saunders, Philadelphia, 1984; pp 263-331. The formation of adhesions between the tendon and surrounding tissue reduces the ability of the repaired tendon to glide normally. This limits post-operative rehabilitation as a result of a reduction in range of motion and an increase in inflammatory pain.

A product which would effectively inhibit fibroblast formation, scarring and adhesion formation can be useful for treating ruptured and otherwise injured tendons.

Current measures for treating excess scarring and adhesions on traumatized tendons include bovine collagen wraps, sheets of hyaluronic acid and hydroscopic polymers (for example; polyethylene glycol) based barriers. In published clinical studies, none of these approaches have shown to consistently reduce the incidence of adhesions or scar formation following repair of tendon injury.

The amnion is a thin, cellular, extra-embryonic membrane that forms the inner membrane of a closed sac surrounding and protecting an embryo in reptiles, birds, and mammals. The sac contains the fetus and amniotic fluid or liquor amnii, in which the embryo is immersed, nourished and protected. Typically, the amnion is a tough, transparent, nerve-free, and nonvascular membrane consisting of two layers of cells: an inner, single-cell-thick layer of ectodermal epithelium and an outer covering of mesodermal, connective, and specialized smooth muscular tissue. In the later stages of pregnancy, the amnion expands to come in contact with the inner wall of the chorion creating the appearance of a thin wall of the sac extending from the margin of the placenta. The amnion and chorion are closely applied, though not fused, to one another and to the wall of the uterus. Thus, at the later stage of gestation, the fetal membranes are composed of two principal layers: the outer chorion that is in contact with maternal cells and the inner amnion that is bathed by amniotic fluid.

The amnion has multiple functions, i.e., as a covering epithelium, as an active secretary epithelium, and for intense intercellular and transcellular transport. Before or during labor, the sac breaks and the fluid drains out. Typically, the remnants of the sac membranes are observed as the white fringe lining the inner cavity of the placenta expelled after birth. The amnion can be stripped off from the placenta. The amnion has a basement membrane side and a stroma side. The fetal membrane including amnion and chorion has been used in surgeries documented as early as 1910. See Trelford et al., 1979, *Am J Obstet Gynecol*, 134:833-845. Amnioplastin, an isolated and chemically processed amniotic membrane, was used for continual dural repair, peripheral nerve injuries, conjunctival graft and flexor and tendon repair. See e.g., Chao et al., 1940, *The British Medical Journal*, March 30. The amnion has been used for multiple medical purposes, e.g., as a graft in surgical reconstruction forming artificial vaginas or over the surgical defect of total glossectomy, as a dressing for burns, on full-thickness skin wounds or in omphalocele, and in the prevention of meningo-cerebral adhesions following head injury or tissue adhesion in abdominal and pelvic surgery.

In 1962, the fetal membrane was used to treat pelvic basins after total exenteration in dogs, however, trials in human proved disappointing.

In recent years, there have been renewed interests in the application of amnion in ocular surface reconstruction, for example, as an allograph for repairing corneal defects. See, for example, Tsai and *Tseng, Cornea.* 1994 September; 13(5):389-400; and Dua et al., *Br. J. Ophthalmol* 1999, 83:748-20 752. In addition, amnion and amniotic fluid have recently been used as sources of placental stem cells. See, e.g., U.S. Pat. No. 7,255,879 and WO 200073421.

The role of the amniotic membrane was investigated in chickens with regard to the prevention of adhesion formation following tendon repair in zone II. Results of histologic examination demonstrated that use of the amniotic membrane significantly reduced the amount of adhesion compared with the other groups. Three months after implantation no remnants of amniotic membrane could be identified at the tendon repair site. Demirkan et al., *Archives of Orthopaedic and Trauma Surgery,* 2002, 122:396-399.

Despite the clinical and published record regarding the safety and efficacy of amnion in broad surgical use, issues regarding reproducibility, safety and the precise form of amnion for each prospective indication have prevented amnion from achieving broad commercial distribution.

There is a need of improved methods and products that would effectively inhibit fibroblast formation, scarring and adhesion formation in treating ruptured and otherwise injured tendons. The present invention relates to such improved methods and products.

BRIEF SUMMARY OF THE INVENTION

In one general aspect, the present invention relates construct for use in surgical repair of tendon, the construct comprising an allograft comprising at least one layer of human amnion and chorion tissues, wherein the allograft is generally cylindrical with a C-shaped cross-section to allow for ease of implantation over the tendon.

In another general aspect, the present invention relates to a method of preparing a construct for use in surgical repair of tendon, the method comprising drying an allograft comprising at least one layer of human amnion and chorion tissues on a frame of a cylindrical shape, wherein the allograft is generally cylindrical with a C-shaped cross-section to allow for ease of implantation over the tendon.

Another general aspect of the invention relates to a method of performing surgical repair of a diseased or damaged tendon in a subject, the method comprising:
 (a) surgically repairing the diseased or damaged tendon to obtain a surgically repaired tendon in the subject; and
 (b) applying a construct according to an embodiment of the present invention over the surgically repaired tendon prior to wound closing.

Yet another general aspect of the invention relates to a kit, comprising:
 (a) a construct for use as a replacement cover for tendon sheaths; and
 (b) instructions for using the construct in surgical repair of tendon,
wherein the construct comprises an allograft comprising at least one layer of human amnion and chorion tissues, wherein the allograft is generally cylindrical with a C-shaped cross-section to allow for ease of implantation over the tendon.

In a preferred embodiment of the present invention, the human amnion and chorion tissues used in the present invention are obtained by a process comprising:
 (a) obtaining informed consent from pregnant females;
 (b) conducting risk assessment on the consented pregnant females to select an amnion donor;
 (c) procuring after birth placenta from the amnion donor; and
 (d) obtaining the human amnion and chorion tissues from the placenta.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
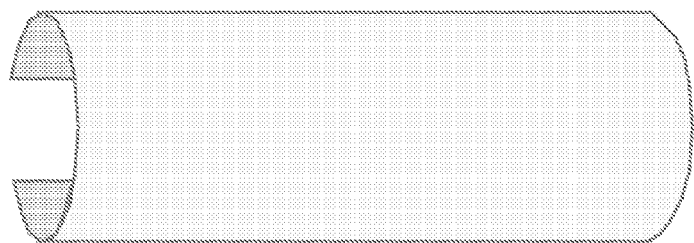
FIG. 1 illustrates a construct for use in surgical repair of tendon according to an embodiment of the present invention.

Unless defined otherwise, all technical and scientific terms used herein have the same meaning as commonly understood to one of ordinary skill in the art to which this invention pertains. In this application, certain terms are used, which shall have the meanings as set in the specification. It must be noted that as used herein and in the appended claims, the singular forms "a," "an," and "the" include plural reference unless the context clearly dictates otherwise.

In one general aspect, embodiments of the present invention relate to a construct for use in surgical repair of tendon, for example as a replacement cover for tendon sheaths. The construct comprises an allograft comprising at least one layer of human amnion and chorion tissues, wherein the allograft is generally cylindrical with a C-shaped cross-section to allow for ease of implantation over the tendon. The construct can be rigid, semi rigid or flexible. In a particular embodiment, a construct according to the present invention is rigid or semi rigid.

In one embodiment of the present invention, the construct further comprises a cylindrical frame. The thickness of the frame can be between 0.5 mm to 2 mm and the length and circumference are the same as the tissue bonded to it. The frame can be rigid, semi rigid or flexible. In a particular embodiment, a construct according to the present invention further comprises a rigid or semi rigid frame.

In one embodiment, the frame is disposable. In another embodiment, the frame is implantable and resorbable. The construct covers a tendon and then adheres to the tendon by rehydration. When an implantable and resorbable frame is used, in the case of either dry, wet or frozen allograft tissues, it allows the allograft membrane to be implanted over injured tendons.

In another general aspect, embodiments of the present invention relate to a method of preparing a construct for use in surgical repair of tendon, for example, as a replacement cover for tendon sheaths. The method comprises drying an allograft comprising at least one layer of human amnion and chorion tissues on a cylindrical shaped frame.

In an embodiment of the present invention, when a disposable frame is used, the dried tissue retains its cylindrical shape when removed from the frame or could be packaged and sterilized with a disposable frame to retain its shape prior to use. The disposable frame can be removed and discarded prior to the use of the tissue. The disposable frame can be longer than the tissue for ease of handling and removal.

In another embodiment of the present invention, the allograft in the replacement cover is reinforced with an implantable and resorbable rigid, semi rigid or flexible polymer frame of a cylindrical shape. This implantable and resorbable frame could be a mesh or a solid frame with several holes throughout.

The allograft, such as human allograft comprising one or more layers of amnion and/or chorion tissues, are bonded to the frame by various methods in view of the present disclosure, such as, drying the tissue on the frame, keeping the tissue wet and laying it on the frame, or freezing the tissue on the frame.

The cylindrical shape, for all configurations mentioned above, can be of various lengths and circumferences to fit the various tendons in the body (see FIG. 1). The circumference of the allograft can be slightly greater than half a full circle to allow ease of implantation. The circumference of the allograft can be larger than the tendon it will be implanted on so that when hydrated it will fully encase the tendon. For example, an allograft construct having a circumference of approximately 81.7 mm (13 mm diameter) or greater might be used for a tendon having a circumference of approximately 62.8 mm (10 mm diameter). In an embodiment of the present invention, the length of the tissue is approximately equal to 2 times the circumference of the tissue.

Another general aspect of the present invention relates to a method of using a construct according to embodiments of the present invention in a surgery treatment of a diseased or damaged tendon. According to an embodiment of the present invention, the construct is placed over, preferably wrapped around, the tendon after surgical repair of the diseased or damaged tendon during the surgery or clinical procedures. The diseased or damaged tendon can be, for example, tibial tendon, peroneus brevis, longus tendons, etc. The method can further comprise treating the subject with one or more additional therapy for the diseased or damaged tendon, such as physical therapy, NSAIDs, etc.

The tendinous structures include, but are not limited to, those tendons that are being repaired with an underlying etiology of: tendinopathy, tendinitis, tendinosis, tenosynovitis, intrasubstance tendon ruptures, or complete tendon ruptures. Examples of tendon rupture include, but are not limited to, Achilles tendon rupture, patellar tendon rupture, or biceps tendon rupture, which can all be surgically repaired using a method according to an embodiment of the present invention.

The surgery can be open surgery or percutaneous surgery. For example, during an open surgery, an incision is made in the skin over the identified rupture site, such as the back of the leg for Achilles tendon rupture. The tendons are retracted for inspection. The ruptured tendon ends are then stitched or sewn together. A cylindrical shaped replacement cover for tendon sheaths according to an embodiment of the present invention is placed on or around the stitched injured tendon then hydrated. When possible, the tendon can be lifted for ease of tissue placement. After hydration, the tissue will adhere to the tendon. Methods of the present invention also apply to a percutaneous surgery, where several small incisions rather than one large incision are made in the skin over the identified rupture site.

In one embodiment of the present invention, a construct according to an embodiment of the present invention is used in surgery treatment of posterior tibial tendon dysfunction (PTTD). The early diagnosis and treatment of PTTD is paramount to preventing progression of deformity. PTTD has been diagnosed more often over the past several years. This is likely a result of this condition having been misdiagnosed or at least under-diagnosed previously. A recent increase in the reporting of this condition in the literature has made its signs and symptoms more easily recognizable.

The posterior tendon's main function occurs during the stance phase of gait where at heel strike it aids in resisting and slowing rearfoot eversion. As the foot progresses into midstance the tendon helps lock the midtarsal joint and begins contracting to cause subtalar joint inversion. Finally, in the propulsive phase of gait the tendon accelerates subtalar joint inversion and in heel lift. So simply put the posterior tibial tendon is the main inverter of the foot and is largely responsible for maintaining arch height. There has been some controversy as to the cause of posterior tendon dysfunction. It generally involves a degeneration of the tendon from a multitude of causes. The overall cause is usually multifactorial in nature. Some structural abnormalities, alone or in combination, which may lead to its development include an accessory navicular, rigid or flexible flatfoot, and equinus. Along with a theory regarding the zone of relative dysvascularity within the tendon between the medial malleolous and the tendon insertion, the aforementioned, leads to degeneration within the tendon. As the tendon degenerates it begins to slowly elongate and eventually loses mechanical advantage. This loss of mechanical advantage allows the peroneus brevis to gain advantage and causes loss of arch height and midtarsal joint break.

Various classifications and staging systems have been proposed for the progression of the deformity. Stage 1 is considered an asymptomatic period where the patient has nothing more than an underlying structural or anatomic abnormality that predisposes them to the development of posterior tendon dysfunction. As the patient progresses into stage 2 they usually develop symptoms that lead to seeking medical attention. Symptoms include tendinitis, some effusion behind the medial malleolous, and progression of a flat foot deformity. The patient will have tenderness along the course of the tendon, abduction of the forefoot, and failure to successfully rise up on their toes on one side. Stage 3 is similar to the 2nd stage with more disabling symptoms and greater degeneration within the tendon be it longitudinal tears or partial ruptures. Finally in stage 4 the patient begins to experience joint adaptation and functional disability.

Diagnosis of PTTD can generally be made on the patient's history and a good clinical exam. Radiographs can be useful to assess joint adaptations in later stages of dysfunction and are useful in surgical planning. The MRI has become a useful tool to assess the pathology within the tendon, that is, whether a simple tenosynovitis exists or whether the dysfunction has progressed to midsubstance tears and partial ruptures. This again may aid in surgical planning.

Treatment is generally based on the stage of dysfunction. Mild stage 1 dysfunction can in certain cases be treated conservatively. The underlying biomechanical abnormality must be controlled to prevent further progression of the deformity. This is generally accomplished with some type of orthotic device with a high degree of varus posting. NSAID's and physical therapy may have some benefit as well. Once the dysfunction progresses into the later stages surgery becomes the only viable option. Surgical intervention starts with direct tendon repair and progresses into tendon transfers and finally to bony reconstruction including calcaneal osteotomies, subtalar arthroereisis procedures, with the last step being a triple arthrodesis.

In another embodiment of the present invention, a construct according to an embodiment of the present invention is used in surgical repair of tendo Achilles rupture.

Posterior superior heel pain can encompass many entities. A thorough history and physical, as well as the utilization of radiographic examination such as plain film radiography, bone scan, and MRI can help narrow a differential diagnosis. The diagnosis of chronic Achilles tendon tear is based on the patient's symptoms, the physical exam and many times magnetic resonance imaging. There are several hypotheses regarding the cause of Achilles tendon rupture. Intratendinous steroid injections, mucoid degeneration degeneration and micro tears within the tendon, intensive physical training without proper warm-up, chronic tendinous inflammation or tenosynovitis, and retrocalcaneal spurring are some of the more recognized etiologies that have been linked to Achilles tendon rupture.

When the diagnosis of chronic Achilles tendon rupture is made the physician must then implement a treatment course. Conservative therapy is often utilized first, which often consists of a combination of NSAIDS, rest, physical therapy (such as phonophoresis, prorprioceptive exercises, ultrasound, ice, whirlpool), accommodative padding, heel lifts, and functional orthotics. If conservative care is exhausted without any significant relief in symptoms, then surgical intervention is usually employed.

The present invention overcomes shortcomings of the prior art by making human amniotic allograft membranes usable as surgical implants to repair damaged tendon sheaths during surgery.

While not wishing to be bound by theory, it is believed that unique properties of amniotic membrane tissue make it ideal for the prevention of tendon adhesion to surrounding tissues. Unlike collagen-based dressings which are biological inert, amniotic membrane tissue has biological properties that are advantageous to its use for tendon repair surgery. These properties include anti-fibrosis, anti-scarring, anti-inflammatory, and anti-microbial, in addition to low immunogenicity. See Niknejad et al., 2008, *Eur Cell Mater,* 29:88-99. Amniotic membrane reduces scar formation by down-regulating transforming growth factor (TGF)-β and its receptor expression on fibroblasts. Tseng et al., 1999, *J Cell Physiol,* 179:325-335; Lee et al., 2000, *Curr Eye Res* 20:325-34. Since fibroblasts require TGF-β to be activated, this down-regulation results in a reduction in fibroblast activity and fibrosis formation and improved tissue reconstruction. Amniotic membrane tissue has been shown to have anti-microbial properties and reduces the risk of post-operative infection as a result of its ability to produce β-defensins. King et al., *Placenta* 2007; 28:161-9. β-defensins are anti-microbial peptides which specifically help epithelial surfaces resist microbial colonization. See Harder et al., 2000, *Am J Respir Cell Mol Biol* 22:714-21; and Krisanaprakornkit et al., 1998, *Infect Immun,* 66:4222-8.

Amniotic membrane tissue also produces secretory leukocyte proteinase inhibitor (SLPI) and elafin. See King above; and Buhimschi et al., 2004, *Am J Obstet Gynecol,* 191:1678-87. In addition to their anti-inflammatory properties, elafin and SLPI both have anti-microbial actions and act as components of the immune system to provide protection from infection. King et al., 2001, *J. Clin Endocrinol Metab,* 88:4426-31. Amniotic membrane tissue has anti-inflammatory properties as a result of its ability to markedly suppress the expression of the potent the pro-inflammatory cytokines, IL-1α and IL-1β. Solomon et al., 2001, *Br J Ophthalmol,* 85:444-9. In addition, amniotic membrane tissue produces natural inhibitors of matrix metalloproteases (MMPs) expressed by infiltrating polymorphonuclear cells and macrophages. Hao et al., 2000, *Cornea,* 19(3):348-52; Kim et al., 2000, *Exp Eye Res.* 70(3): 329-37).

Repairing ruptured tendons requires the surgeon to work in very tight spaces and repairing the tendon sheath is extremely difficult. Surgeons who attempt to repair the tendon sheath with a replacement membrane encounter several problems. The prior art uses bovine collagen sheets, hyraluronic acid sheets or hydrophilic and resorbable polymer sheets. Curving a flat sheet around a tendon at the surgical site is extremely difficult for the surgeon and even if successful, the resulting barrier is effective at preventing scarring and adhesions less than 50% of the time according to published peer reviewed literature.

By creating a cylindrical shape which mimics the size and characteristics of a human tendon from human allograft amnion and/or chorion membrane material which has the ability to reduce adhesions, scar formation while also reducing inflammation and risk of post-operative infection we have created a significant improvement over prior art.

Moreover, amniotic tissue used in embodiments of the present invention is prepared from birth tissue procured from a pregnant female using a well controlled process. Informed consent is obtained from a pregnant female by following guidelines as promulgated by the American Association of Tissue Banks and consistent with guidelines provided the Food and Drug Administration: a federal agency in the Department of Health and Human Services established to regulate the release of new medical products and, finally, if required by an established review body of the participating hospitals or institutions. The pregnant female is informed that she will be subject to risk assessment to determine if she is qualified as a birth tissue donor. She will also be informed of the tests for the risk assessment. The pregnant female is further informed that, if she is selected as a birth tissue donor based on the risk assessment, her birth tissues, such as placenta and amniotic fluid, may be collected at birth, tested and processed for medical uses.

The informed consent includes consent for risk assessment and consent for donation of birth tissues.

Risk assessment is conducted on a pregnant female with informed consent to evaluate her risk factors for communicable diseases, such as human immunodeficiency virus (HIV), hepatitis B virus (HBV), hepatitis C virus (HCV), cytomegalovirus (CMV), human T-lymphotropic virus (HTLV), syphilis, etc. Medical and social histories of the pregnant female, including physical exam record, and/or risk assessment questionnaire, are reviewed. Pregnant females with high risk factors for the communicable diseases are excluded.

Consent to draw blood at time of delivery and 1 to 12 months post delivery is obtained from pregnant females with low risk factors for the communicable diseases. Screening tests on communicable diseases, such as HIV 1 and 2, HCV, HbCore, syphilis, HTLV I/II, CMV, hepatitis B and C, are conducted by conventional serological tests on the blood sample obtained at birth. The initial screening tests are preferably completed within 7 days after birth. Preferably, the screening tests are conducted again on a second blood sample collected a few months post delivery, to verify the previous screening results and to allow for detection of communicable disease acquired shortly before birth, but are shown as "negative" on the previous screening tests. The second blood sample can be collected 1-12 months, preferably 6 months, post birth.

Only pregnant females with informed consent who are tested negative for the communicable diseases are approved as birth tissue donor. In a preferred embodiment, only pregnant females with informed consent who are tested negative for the communicable diseases in both screening tests with the blood sample drawn at birth and the blood sample drawn 6 months post delivery are approved as birth tissue donor.

Sterile techniques and procedures should be used as much as practically possible in tissue handling, e.g., during tissue procurement, banking, transfer, etc., to prevent contamination of the collected tissues by exogenous pathogens.

Only birth tissues procured from the approved birth tissue donors are subject to the collection and subsequent processing. Birth tissues, such as placenta and amniotic fluid, are recovered from the delivery room and are transferred to a location in a sterile container, such as a sterile plastic bag or bottle. Preferably, the tissues are transferred in a thermally insulated device at a temperature of 4° to 28° C., for example, in an ice bucket.

According to an embodiment of the invention, shortly after its expulsion after birth, a suitable human placenta is placed in a sterile bag, which is placed in an ice bucket, and is delivered to another location. The placenta is rinsed, e.g., with sterile saline, to removed excessive blood clots. Preferably, the placenta is subject to aseptic processing, for example, by including one or more antibiotics, such as penicillin and/or streptomycin, in the rinse. The aseptically processed placenta is stored in a controlled environment, such as hypothermic conditions, to prevent or inhibit apoptosis and contamination.

The processed placenta is placed in a sterile container, such as one made of triple sterile plastic bags, packed in wet ice, and shipped to a location for subsequent processing via overnight courier. The placenta is shipped together with release documents for processing. For example, each shipment must include technical approval to process based upon a satisfactory review of the criteria for donor selection and donor approval. The shipment must also include results on screening of communicable diseases. Preferably, the shipment includes medical director review and approval of donor eligibility/suitability.

Upon receiving the shipment and a satisfactory review of the accompanying release documents, the amnion is separated from the chorion and other remaining tissues of placenta using methods known in the art in view of the present disclosure. For example, the amnion can be stripped off mechanically from the placenta immersed in an aseptic solution, e.g., by tweezers. The isolated amnion can be stored in a cryoprotective solution comprising a cryoprotective agent, such as dimethyl sulfoxide (DMSO) and glycerol, and cryopreserved by using a rapid, flash-freeze method or by controlled rate-freeze methods. Preferably, the isolated amnion is treated with one or more antibiotics, such as penicillin and/or streptomycin, prior to cryopreservation. The chorion can also be separated from the other tissues, preserved and stored for future use.

The isolated amnion is a tough, transparent, nerve-free and nonvascular sheet of membrane. It can be dried or lyophilized using various methods. For example, it can be dried over a sterile mesh, for example, by being placed on a sterile nitro-cellulose filter paper and air dried for more than 50 minutes in a sterile environment. It can also be dried or lyophilized over other form of supporting material, which would facilitate the subsequent manipulation of the amnion, such as sterilizing, sizing, cataloging, and shipping of the amnion.

The following examples illustrate the invention but are in no way intended to limit the scope of the present invention.

Example 1

This example illustrates a surgical procedure for the application and wrapping of a tendon with a construct of the present invention.

The application of the allograft construct commences upon completion of repair to the tendon. Repair to the tendon and its structures can include, but are not limited to, synovectomy, tendon tubularization, debridement of the tendon, retinacula repair, sheath repair or end-to-end anastomosis. The cylindrical allograft construct is typically about 8 mm to 10 mm in diameter and has a length of about 60 mm.

The tendon, being exposed, is now ready for the application of the construct. The sheath is either opened temporarily by the use sutures or with skin hooks. The sutures are placed adjacent to the tendon repair site, on opposing sides of the tendon and another set of sutures proximal to the first set of sutures. Alternatively, this can also be accomplished by an assistant holding the sheath open with skin hooks. The tendon is gently lifted up and out of the tendon groove with blunt, curved retractors, similar to a Senn or McBurney retractor. The retractors are placed on both sides of the tendon defect. The retractors are far enough away from the defect to allow the cylindrical allograft to insert without touching the retractors. The cylindrical allograft is opened by separating the two sides and pulling the cylindrical allograft apart; with blunt forceps, the opening is wide enough to pass over the tendon. With the assistant holding the tendon stationary, the cylindrical allograft is placed over the tendon. The cylindrical allograft is to be kept dry until delivered to the tendon. Upon application, the cylindrical allograft closes around and on the tendon, creating a wrap, and the tendon adheres to the allograft by surface tension. An optional step can be introduced by tacking down the proximal and distal ends of the cuff to the tendon with #6-0 absorbable suture. With the cylindrical allograft in place, the tendon is returned to the tendon groove by the retractors. The retractors are then rotated off and away from the tendon, leaving the tendon to rest in the groove with the amniotic membrane covering. The sheath, if present, along with soft tissue is approximated and sutured. The retention sutures attaching to the sheath are cut. Upon final closure of the sheath, the area is irrigated with sterile saline.

Example 2

This example illustrates the application of an allograft construct according to an embodiment of the present invention during surgical treatment of posterior tibial tendon dysfunction (PTTD).

The patient was a 47-year-old woman who presented with a complaint of tenderness in the medial aspect of her right ankle which also occasionally radiated distally into her foot for a period of 6 months. The patient indicated that the pain increased during ambulation and prolonged periods of activity. According to the patient, the pain was not related to any trauma to the foot. The patient noted that she had experienced a progressive flattening of her arch over the past few months. Self-prescribed acetaminophen and ibuprofen did not provide pain relief. The patient's medical history revealed hypertension treated with a beta blocker, no previous surgeries and no known drug allergies.

Upon physical exam the patient had considerable tenderness along the course of the posterior tibial tendon, from just behind the medial malleolous to its insertion into the navicular. There appeared to be a normal range of motion of the ankle joint as well as the subtalar and midtarsal joints. Manual muscle testing revealed all groups to be full strength except for some weakness of the foot on resistance against inversion with some pain as well during this maneuver. On standing the patient appeared to have an abducted forefoot on the rearfoot especially on the right foot. The patient also had an obvious inability to rise up on her toes on the right foot.

MRI demonstrated a thickening of the tibialis posterior tendon. There was an increase signal circumferentially with tendon sheath effusion. The intratendinous signal was also increased. Radiographs in the lateral view demonstrated a loss in the longitudinal arch with a first ray elevatus and break in the cyma line. The talus was plantarflexed and the calcaneal inclination approached the parallel weight-bearing surface. No osteoarthritic findings were noted.

Based on the patient history, physical exam and imaging results a diagnosis of posterior tibial tendon dysfunction was made.

Figure 2:
FIG. 2 is a photograph of posterior tibial tendon exposed during surgery repair of tibialis posterior tendon dysfunction (TPTD)

Based on the patient diagnosis and progression of her condition, a decision was made to surgically repair her posterior tibial tendon. After the patient was appropriately prepped and an initial incision was made, the posterior tibial tendon sheath was identified and incised (FIG. 2). The tendon was noted to have marked adhesions and vinculae attachments connecting the tendon to the entire sheath from the medial malleolus and distally to the insertion at the medial tuberosity of the navicular. All of the adhesions, vinculae were removed and the surface tears of the tendon were excised.

The tendon was inspected into the central intra-substance body and the entire necrotic tendon present was surgically removed. The tendon was then closed in an inverted tubular fashion with 4-0 absorbable suture. The internal surface presented with a marked amount of reactive sinusitis tissue, this was derided.

Figure 3:
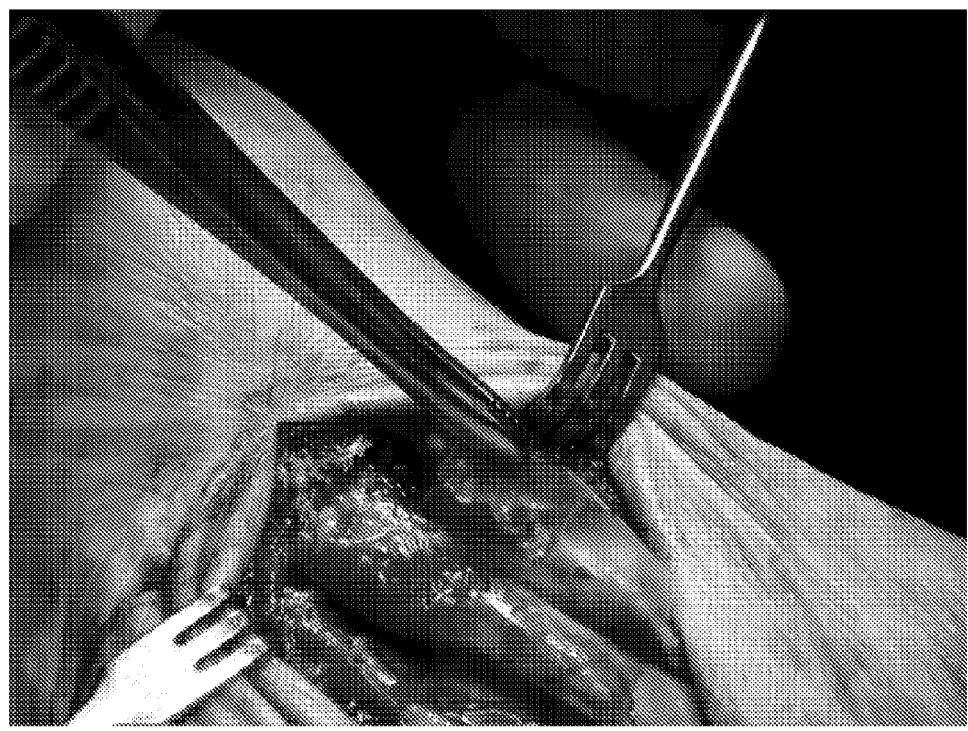
FIG. 3 is a photograph illustrating the application of an amniotic allograft construct according to an embodiment of the present invention to posterior tibial tendon following tendon repair during the surgery treatment of TPTD.
Figure 4:
FIG. 4 is a photograph illustrating the posterior tibial tendon wrapped with an amniotic allograft construct according to an embodiment of the present invention prior to wound closing during the surgery treatment of TPTD.

The repaired tendon was then wrapped with amniotic membrane tissue to prevent tendonsheath interface adhesion and reduce the risk of inflammation (FIG. 3). The membrane was wrapped directly around the tendon in the area of suspected adhesion, the excess was cut with tenotomy scissors (FIG. 4). The material adheres by surface tension and quickly reconstitutes and rehydrates and obviates the need for suturing.

The sheath was closed with 4-0 absorbable and deep closure with 2-0 absorbable and skin with 4-0 absorbable suture followed by the application of a dry sterile dressing.

The patient was placed into a below the knee cast for 3 weeks, followed by a cam walker. Physical therapy to increase strength and motion started on the $4^{th}$ week. The patient continued to ambulate without assistance and has minimal discomfort.

Example 3

This example illustrates the application of an allograft construct according to an embodiment of the present invention during surgical treatment of chronic total tendo-Achilles rupture.

The patient was a 55-year-old man who presented with a five-month history of posterior superior right heel pain. The patient noticed occasional sharp shooting pain in his right heel that began as remitting but eventually progressed to constant tenderness approximately 3-4 weeks after the onset of initial symptoms. Irritating pain, swelling, and tenderness were present with both ambulation and non-weight bearing, but were aggravated with activity. The patient denied any precipitating activity or history of trauma to the area. Self treatment consisted of anti-inflammatory medication.

Upon examination, the patient's tendo-Achilles was indurated and swollen with an increase in the diameter of the right ankle as compared to the left. The patient experienced pain upon palpation of the posterior superior aspect of right Achilles tendon at its insertion that traveled proximally 15 cm. The patient had a palpable defect and separation in the tendoachilles with an increase in separation when the foot was dorsiflexed. He also had a non-tender plantar fascia or plantar medial tubercle of calcaneus with no signs of crepitus on range of motion of the right Achilles tendon. The patient had discomfort with dorsiflexion and plantarflexion of the right ankle posteriorly, and manual muscle testing of lower extremity yielded a decreased plantarflexory power of the right ankle.

T2 weighted MRI images of the right ankle and foot showed a lack of homogenicity with multiple intratendinous splits and presence of intratendinous fluid within the Achilles tendon. An increased thickness of Achilles tendon and decrease in signal intensity within the tendon approximately 5-15 cm from Achilles insertional area was observed on T1 weighted images.

Based on the patient history, physical exam and imaging results a diagnosis of chronic total tendo-Achilles rupture was made.

In this case it was obvious that the tendon was disrupted and this obviated the need for conservative care and led to immediate open repair. Surgical treatment typically involves tendon repair and tenolysis. Various surgical techniques and postoperative protocols have been established and refined through the years that have proven to be effective.

Figure 5:
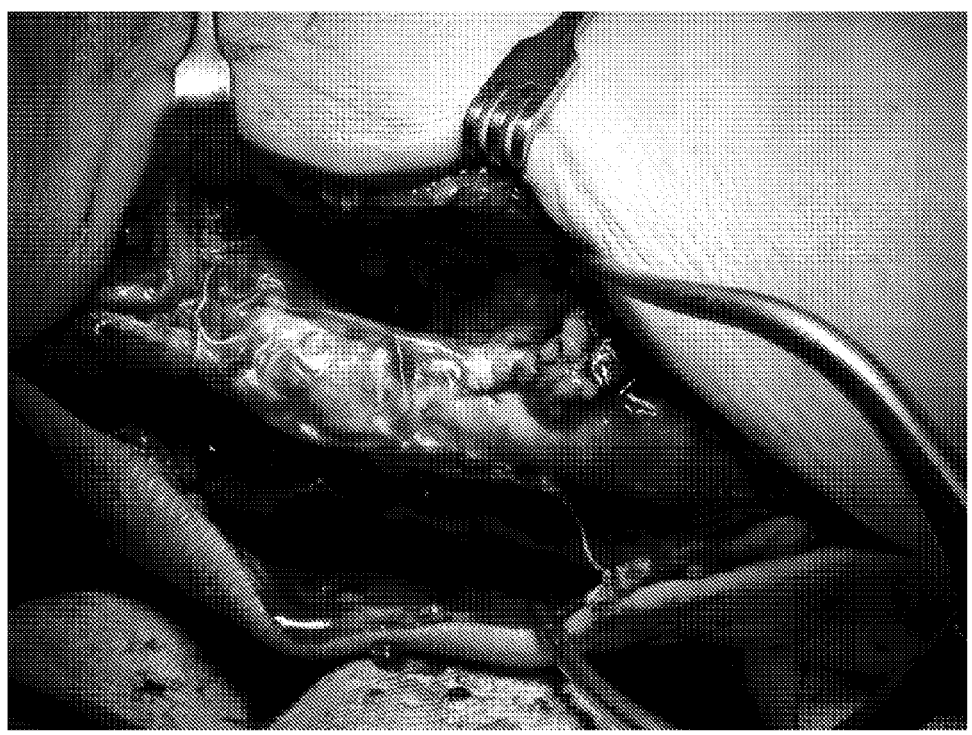
FIG. 5 is a photograph illustrating Achilles tendon wrapped with an amniotic allograft construct according to an embodiment of the present invention prior to closing wound during the surgery treatment of chronic total tendo-Achilles rupture.

After the patient was appropriately prepped, an initial incision was made over the tendo Achilles. In this particular case the entire paratenon and tendon were non-existent in this distal portion of the insertion of the tendon. The markedly contracted tendon was lengthened with a modified gastrocnemius slide via an end-to-end approximation of the tendoachilles. Prior to the anastomosis of the tendon all of the necrotic tendon, soft-tissue and scar formation was excised. Utilization of a medial/lateral Krakow stitch closure was used to join the proximal and distal tendon. Since no remnants of a paratenon or glide mechanism remained in the area of closure, a decision was made to use amniotic membrane tissue to reduce the potential for adhesion formation after closure between the repaired tendon and soft tissues. The amniotic membrane was placed directly on the tendon on the posterior area of suspected tendon adhesion to the soft tissue. The material adheres by surface tension and quickly reconstitutes and rehydrates and obviates the need for suturing (FIG. 5).

Post-operatively the patient was placed into dry sterile dressings and a non-weight bearing above the knee cast for two weeks followed by a three-week below-the-knee cast. At the fifth week a cam walker, non-weight bearing was used for an additional 2 weeks. Physical therapy started at the seventh week to start the patient's ambulation and gradual increase in strengthening and range of motion exercises. The patient tolerated the procedure quite well without complaints of pain and to date his ambulation is proceeding well with good range of motion and strength.

The clinical experiences described in Examples 2 and 3 demonstrated that amniotic membrane tissues can be beneficial when used as a tendon wrap during tendon repair surgery. The demonstrated anti-adhesive, anti-inflammatory and anti-microbial properties of amniotic membrane tissue make this a unique alternative to biologically inert collagen matrix products currently available for use in foot and ankle surgery and possible for tendon repair surgery of the upper extremities. As supplied, the allograft construct according to embodiment of the present invention is easy to apply and does not require a change in surgical technique to use.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of performing surgical repair of a diseased or damaged tendon in a subject, comprising:
    (a) surgically repairing the diseased or damaged tendon to obtain a surgically repaired tendon in the subject; and
    (b) applying a construct comprising an allograft comprising at least one layer of human amnion and chorion tissues over the surgically repaired tendon prior to wound closing,
wherein the construct is generally cylindrical with a C-shaped cross-section to allow for ease of implantation over the tendon.

2. The method of claim 1, wherein the step of surgically repairing comprises at least one selected from the group consisting of synovectomy, tendon tubularization, debridement of the tendon, retinacula repair, sheath repair and end-to-end anastomosis.

3. The method of claim 1, wherein the construct wraps around the surgically repaired tendon prior to wound closing.

4. The method of claim 1, wherein the diseased or damaged tendon is posterior tibial tendon, peroneus brevis, or peroneus longus tendons.

5. The method of claim 1, wherein the diseased or damaged tendon has at least one underlying etiology selected from the group consisting of tendinopathy, tendinitis, tendinosis, tenosynovitis, intrasubstance tendon ruptures, and complete tendon ruptures.

6. The method of claim 1, wherein the subject has a tendon rupture selected from the group consisting of Achilles tendon rupture, patellar tendon rupture and biceps tendon rupture.

7. The method of claim 1, wherein the subject has posterior tibial tendon dysfunction.

8. The method of claim 1, further comprising administering to the subject one or more additional treatments to the diseased or damaged tendon.

9. The method of claim 8, wherein the additional treatment is a nonsteroidal anti-inflammatory drug (NSAID) treatment or a physical therapy.

10. The method of claim 1, wherein the construct further comprises a rigid or semi-rigid frame that is implantable and resorbable.

11. The method of claim 1, wherein the human amnion or chorion tissues are obtained from birth tissue procured from a pregnant female donor, and the human amnion or chorion tissues are selected after conducting a screening test on the donor one to twelve months post-birth.

12. The method of claim 1, wherein the construct is placed over the surgically repaired tendon on the area of suspected tendon adhesion to soft tissue, thereby reducing the potential for adhesion formation after wound closure between the surgically repaired tendon and soft tissue.

13. A method of performing a surgical treatment of an Achilles tendon rupture in a subject, comprising:
    (a) surgically repairing the Achilles tendon to obtain a surgically repaired Achilles tendon, wherein the surgical repair comprises anastomosis of the tendon; and
    (b) applying a dried construct comprising an allograft comprising at least one layer of human amnion and chorion tissues over the surgically repaired Achilles tendon prior to wound closing, such that the dried construct adheres to the tendon by surface tension and rehydrates,
wherein the construct is generally cylindrical with a C-shaped cross-section to allow for ease of implantation over the surgically repaired tendon.

14. The method of claim 13, wherein the construct is not sutured to the tendon prior to wound closing.

15. The method of claim 13, wherein the construct is placed directly on the surgically repaired Achilles tendon over the area of suspected tendon adhesion to soft tissue, thereby reducing the potential for adhesion formation after wound closure between the surgically repaired Achilles tendon and soft tissue.

16. The method of claim 13, wherein the construct further comprises a rigid or semi-rigid frame that is implantable and resorbable.

17. A method of performing a surgical treatment of a tibialis posterior tendon dysfunction in a subject, comprising:
    (a) surgically repairing the tibialis posterior tendon in the subject to obtain a surgically repaired tibialis posterior tendon, wherein the surgical repair comprises incising the posterior tendon sheath to expose the tendon and removing any identified adhesions and surface tears of the tendon; and
    (b) applying a construct comprising an allograft comprising at least one layer of human amnion and chorion tissues over the surgically repaired tendon prior to closing of the tendon sheath,
wherein the construct is generally cylindrical with a C-shaped cross-section to allow for ease of implantation over the surgically repaired tendon.

18. The method of claim 17, wherein the surgical repair further comprises removing vinculae attachments connecting the tendon to the tendon sheath.

19. The method of claim 17, wherein the construct further comprises a rigid or semi-rigid frame that is implantable and resorbable, the construct being dried over the frame, such that the dried construct comprising the frame is applied to the tendon and adheres to the tendon by surface tension without the need for suturing.

* * * * *